US00PP12965P2

(12) United States Plant Patent
Byrne

(10) Patent No.: US PP12,965 P2
(45) Date of Patent: Sep. 17, 2002

(54) PEACH TREE NAMED 'TROPICPEACHONE'

(75) Inventor: David H. Byrne, Bryan, TX (US)

(73) Assignee: The Texas A&M University System, College Station, TX (US)

( * ) Notice: Subject to any disclaimer, the term of this patent is extended or adjusted under 35 U.S.C. 154(b) by 4 days.

(21) Appl. No.: 09/731,392

(22) Filed: Dec. 5, 2000

(51) Int. Cl.[7] ..... A01H 5/00
(52) U.S. Cl. ..... Plt./197

(58) Field of Search ..... Plt./197

*Primary Examiner*—Bruce R. Campell
*Assistant Examiner*—Susan B. McCormick
(74) *Attorney, Agent, or Firm*—Fulbright & Jaworski LLP

(57) ABSTRACT

Disclosed is a new variety of *Prunus persica* named 'TROPICPEACHONE'. This new variety, which requires approximately 150 chilling units of dormancy, is considered to be a peach tree of early season maturity, which produces yellow fleshed fruit that are very firm, attractively colored, and suitable for both local and long-distance shipping.

4 Drawing Sheets

1.0 BACKGROUND OF THE INVENTION

1.1 Field of the Invention

This invention relates to peach trees and, more specifically, to peach trees referred to as a variety of *Prunus persica* named 'TROPICPEACHONE'. 'TROPICPEACHONE', which requires approximately 150 chilling units of dormancy, produces an exceptionally high quality, firm clingstone peach that matures early in the season.

2.0 Summary of the Invention

The 'TROPICPEACHONE' peach is characterized as to novelty and is otherwise noteworthy by producing fruit that ripens in the early season; is considered very high quality; and which is firm and has an attractive coloration. In this regard, the present variety of peach tree bears fruit that are ripe for commercial harvesting and shipment in the last days of May and/or the first days of June, when the fruit is grown in the San Joaquin Valley of Central California. 'TROPICPEACHONE' ripens 7 to 10 days earlier than its parent, 'TropicBeauty' Peach, a non-patented variety (Rouse and Sherman, *HortScience,* 24:165–166, 198). Additionally, the new variety exhibits the potential to be commercialized in regions that have chilling requirements that are relatively low.

2.1 ORIGIN OF THE VARIETY

The present peach tree was the result of an ongoing Stone Fruit Breeding Program of Texas A & M University, College Station, Brazos County, Tex. To this end, both controlled and hybrid crosses are made each year in order to produce seedling populations from which improved progenies are evaluated and selected.

The seedling 'TROPICPEACHONE' was originated at the Texas A & M Citrus Center in Weslaco, Hidalgo County, Tex. in 1994, and was chosen from a population of seedlings that resulted from a controlled cross of the peach 'TropicBeauty', used as the seed parent, and 'TropicBeauty', which was also used as the pollen parent. Resulting seed from this cross were planted in 1992 at the Citrus Center in Weslaco, Tex. 'TROPICPEACHONE' was marked for subsequent observation and noted as having exceptional characteristics. Two-and three-year old trees of the variety were subsequently evaluated during the 1999 and 2000 fruit growing seasons.

2.2 ASEXUAL REPRODUCTION OF THE VARIETY

'TROPICPEACHONE' was bud grafted onto virus-free Nemaguard ("The Brooks and Olmo Register of Fruit and Nut Varieties," 3rd Ed., American Society of Horticultural Science Press, Alexandria, Va., 1997) peach rootstock in May 1997 at a nursery site in Oakdale, Calif. The variety was subsequently planted at the experimental orchard in the central portion of the San Joaquin Valley, near Fowler, Fresno County, Calif. Fruit from the resulting propagation has been evaluated for both the 1999 and 2000 fruit seasons. This evaluation clearly demonstrated that the re-propagated trees were true to the characteristics of the original seedling in all observable aspects.

3.0 PHOTOGRAPHS OF THE VARIETY

This new variety of peach tree is illustrated by the accompanying photographic drawings and depicts the plant by the best possible color representation using color photography, wherein.

Figure 1:
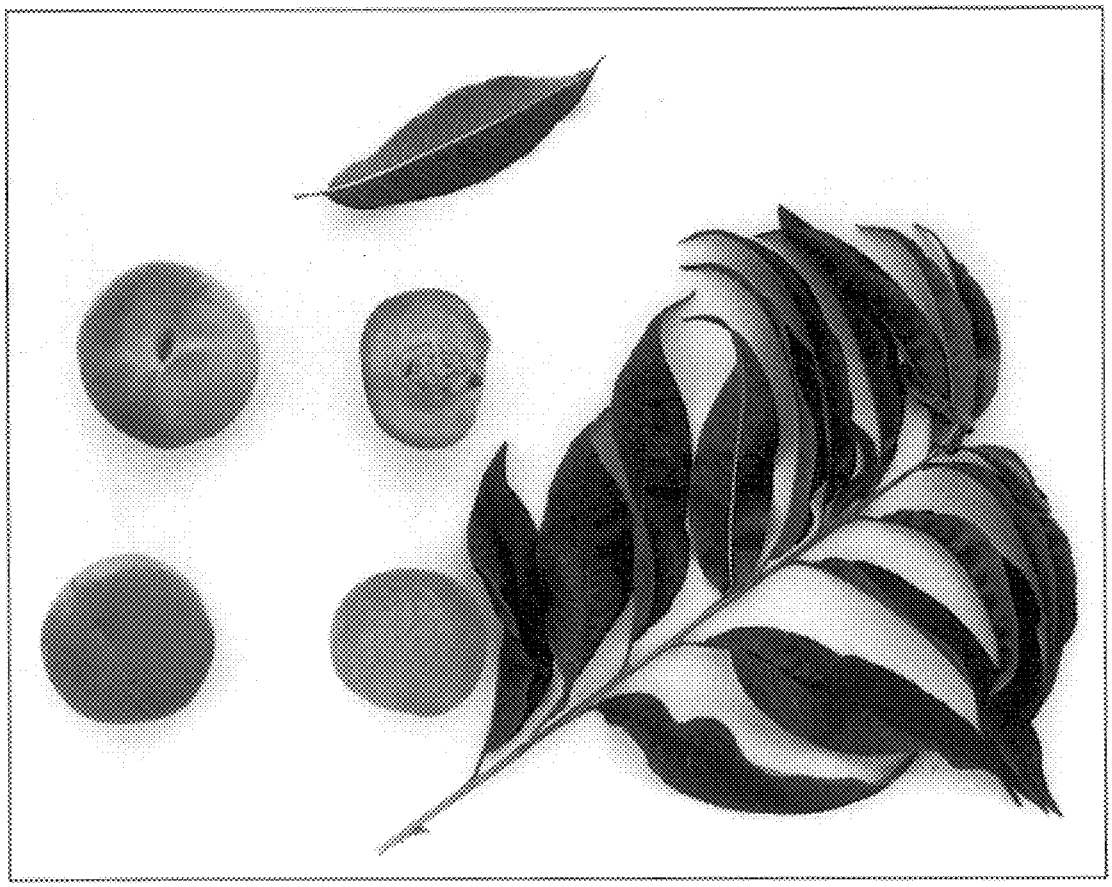
FIG. 1 is a color photograph of a characteristic twig bearing leaves; several leaves showing both the dorsal and ventral coloration, and several mature fruit showing their external coloration sufficiently matured for harvesting and shipment. Additionally one fruit of the subject variety is dissected in the axial or suture plane to illustrate the flesh and stone characteristics thereof.
Figure 2:
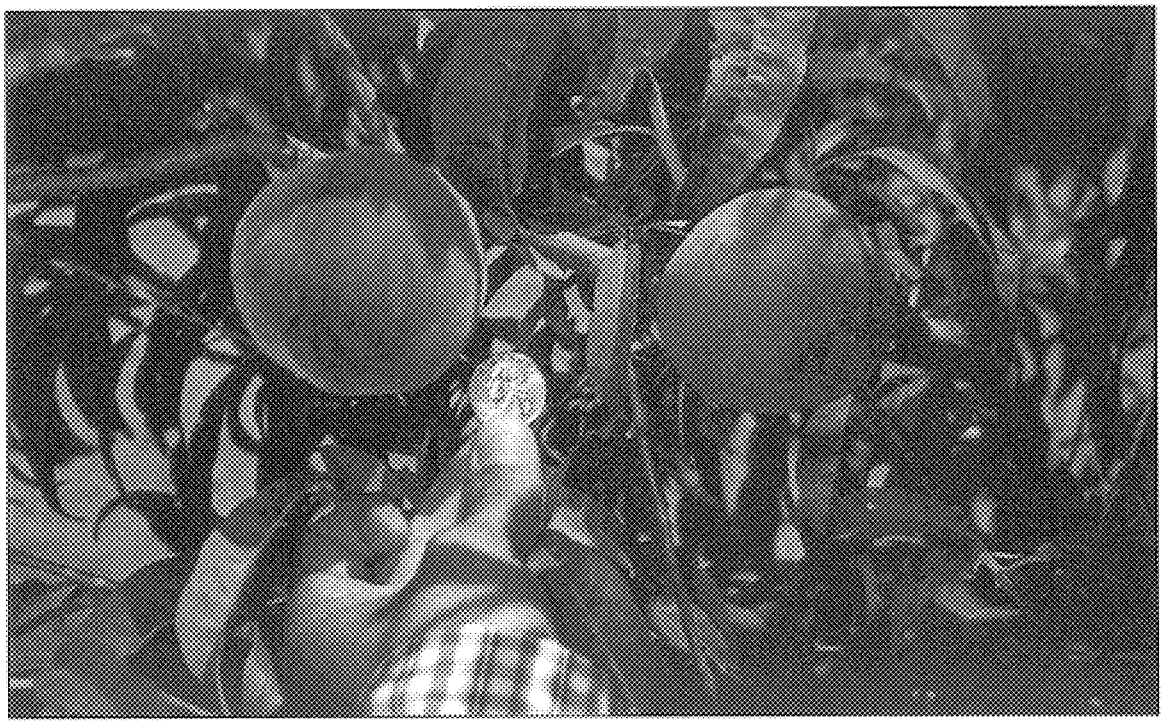
FIG. 2 is a color photograph showing the fruit on a 2-year old 'TROPICPEACHONE' tree grown in Caborca, Sonora, Mexico.
Figure 3:
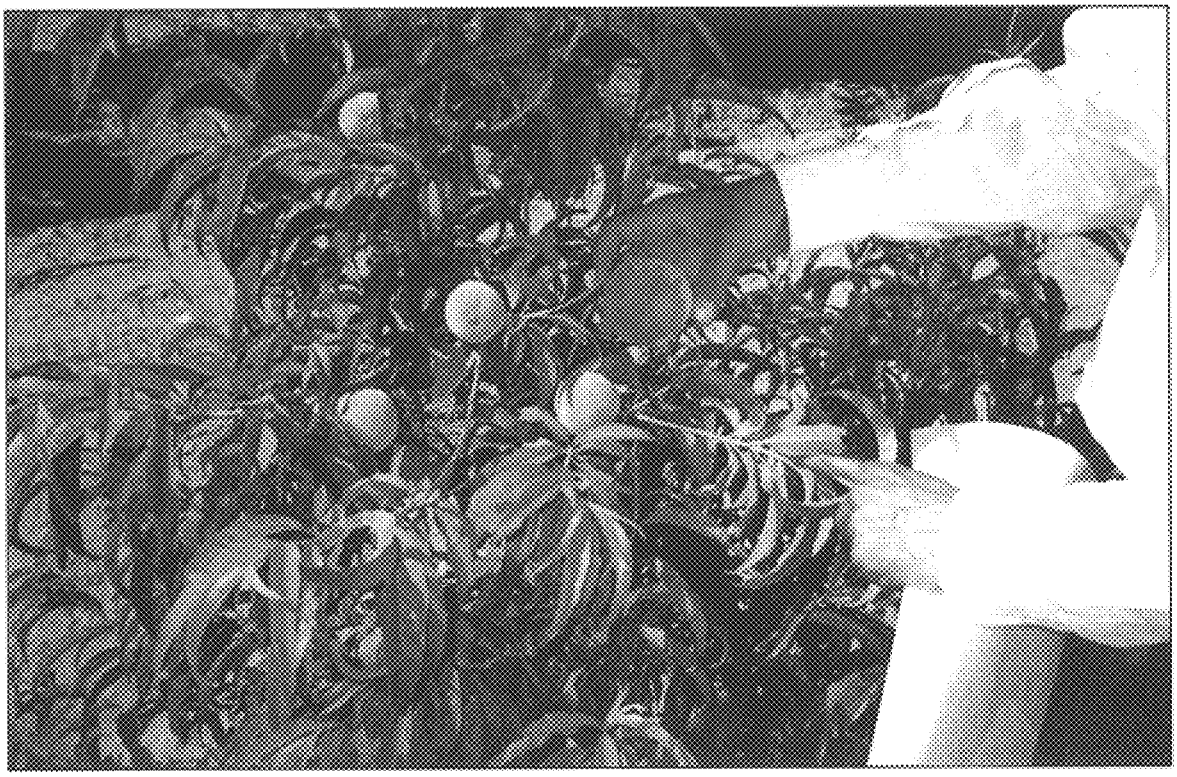

FIG. 3 is a color photograph showing that the fruit from 'TROPICPEACHONE' ripens 7–10 days before that of the parent plant, 'TropicBeauty'. The 'TROPICPEACHONE' fruit is held next to the fruit of 'TropicBeauty'. All fruit were from two-year old trees grown in Carborca, Sonora, Mexico.

Figure 4:
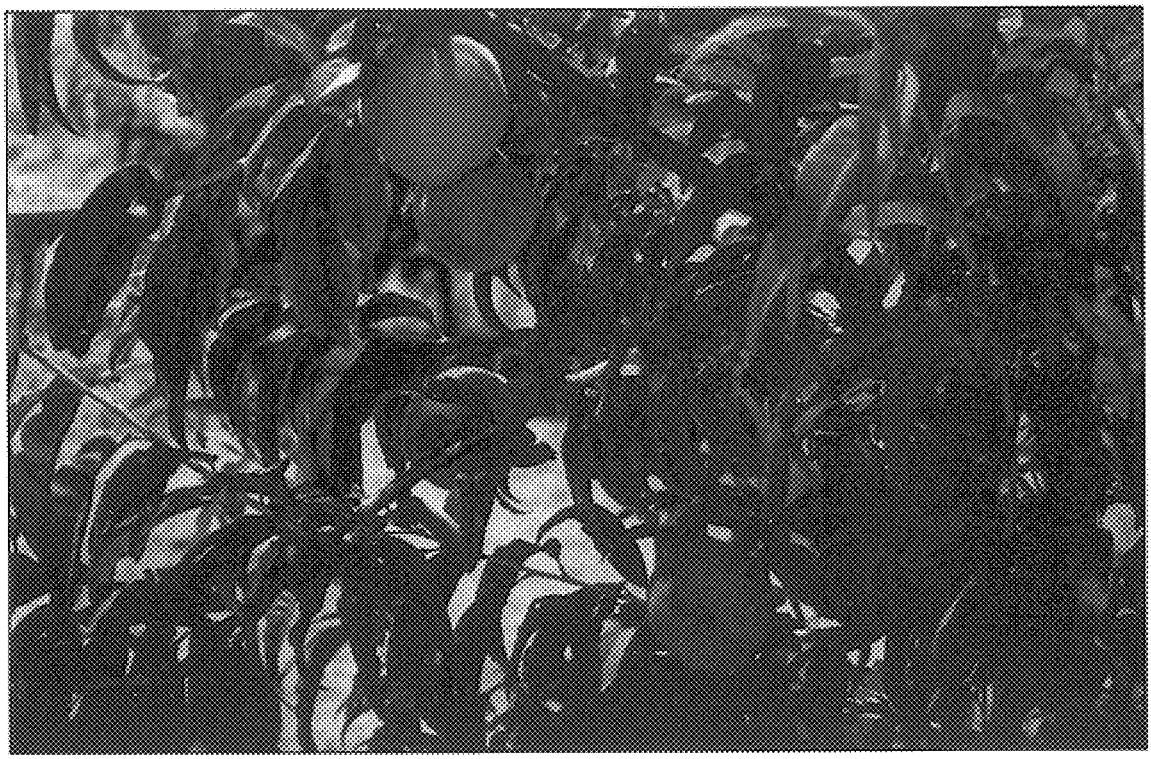

FIG. 4 is a color photograph showing 'TROPICPEACHONE' fruit on a 2-year old tree grown in Caborca, Sonora, Mexico.

4.0 BOTANICAL DESCRIPTION OF THE VARIETY

Referring more specifically to the pomological details of this new and distinct variety of peach tree, the following has been observed under the ecological conditions prevailing at experimental orchards in Fowler, Calif. All major color code designations are by reference to The R.H.S. Colour Chart (Third Edition) provided by The Royal Horticultural Society of Great Britain. Colors are approximate as color depends on horticultural practices such as light level and fertilization rate, among others.

4.1 TREE

Size: Generally average to above average as compared to other common peach cultivars ripening in the early season of maturity.

Height: 8.5 feet (2.58 m) at the end of the 1999 growing season.

Width: 6.2 feet width (1.80 m) at the end of the 1999 growing season.

Vigor: High.

Density: Medium to high.

Productivity: Productive.

Shape: The 'TROPICPEACHONE' peach has been trained in central lead configuration but exhibits a generally spreading and basitonic tropism when compared to average commercial varieties of peach. 'TROPICPEACHONE' grows more upright than 'UFGold' (U.S. Plant Pat. No. 10,315, Apr. 7, 1998) and less upright than either 'TropicBeauty' or 'TropicSnow'.

Current season growth: The current season growth for the new variety was approximately 3.0 to 3.3 feet (0.91–1.12 m).

Regularity of bearing: Regular, and considered hardy under typical central San Joaquin Valley, Calif. conditions.

4.2 TRUNK

Size: Approximately 2.5 inches (6.35 cm) in diameter when measured at a distance of approximately 6 inches (15.25 cm) above the soil level, at the end of the 1999 growing season on a two-year old tree.

Bark texture: Considered moderately rough with numerous folds of papery scarf-like skin being present.

Bark coloration: Variable, but it is generally considered to be a gray-brown (RHS Grey Orange Group 176B).

4.3 BRANCHES

Size: Considered medium for the variety.

Thickness: Average (about 3.1 cm in diameter on a two-year old tree) as compared to other *Prunus persica* varieties.

Surface texture: Average, and appearing furrowed on wood that is several years old.

Lenticels: Numerous flat, oval lenticels present. The lenticels range in size from approximately 2.0 to 6.0 mm in width and from 1 to 2 mm in height.

Current season shoots: Surface texture — Substantially glabrous.

Internode length: Approximately 2.1 to 2.3 cm.

Color of mature branches: The predominant colors are 166C and 200D of the RHS Grey Orange Group.

Current season shoots: Color — Light green (RHS Yellow Green Group 144C) with some reddish-brown coloration appearing on exposed exterior shoots (RHS Grey Red Group 181B). The color of new shoot tips is considered a bright and shiny green (mainly RHS Green Group 141C and 143C).

4.4 LEAVES

Size: Considered moderately large for the species. Leaf measurements have been taken from vigorous upright current season growth approximately at mid-shoot.

Leaf length: Approximately 155 to 170 mm.

Leaf width: Approximately 35 to 42 mm.

Leaf thickness: Approximately 1 to 2 mm.

Leaf form: Lanceolate.

Leaf tip form: Acuminate. The tip often appears flexed downwards and slightly twisted laterally.

Leaf upper surface color: Dark green, varying between RHS Green Group 131A and 137B.

Leaf lower surface color: Medium green, varying between RHS 137C and 141B.

Leaf mid-vein color: Light yellow green (RHS Yellow Green Group 149D).

Leaf margins:

*Form.*—Considered crenate, occasionally doubly crenate.

*Uniformity.*—Considered generally uniform.

Leaf petioles:

*Size.*—Considered medium to medium long.

*Length.*—Approximately 8 to 11 mm.

*Thickness.*—Approximately 1.5 to 2 mm.

*Color.*—Pale green (RHS Yellow Green Group 144D).

Leaf glands:

*Size.*—Approximately 1 mm in height and 1 to 2 mm in width.

*Number.*—Generally one per side, occasionally two per side.

*Type.*—Reniform, considered shallow for the gland type.

*Color.*—Greenish brown (RHS Yellow Green Group 152B).

Leaf stipules:

*Size.*—Medium for the variety.

*Length.*—Approximately 6 to 9 mm.

*Form.*—Lanceolate in form and a serrated margin.

*Color.*—Green (RHS Green Group 141C).

4.5 FLOWERS

Floral buds:

*General.*—The floral buds are considered to be medium to medium large in size, conic in form, and slightly appressed relative to the bearing shoot.

*Color.*—The bud scales are gray-brown, (approximately RHS Grey Orange Group 177D). The buds are considered hardy under typical central San Joaquin Valley, California climatic conditions.

*Length.*—Approximately 17 to 20 mm.

Blooming type: Considered quite early in relation to other peach cultivars commonly growing in the central San Joaquin Valley. Date of full bloom was Feb. 5, 2000.

Flower type: Showy.

Flower size: Flower diameter at full bloom is approximately 37 to 43 mm.

Bloom quantity: Considered abundant.

Flower bud frequency: Normally 1 to 2 per node.

Petal size:
*General.*—Considered medium to medium large for the species.
*Width.*—Approximately 16 to 19 mm.
Petal form: Broadly ovate.
Petal count: Nearly always 5.
Petal color: Light pink when young (RHS Red Purple Group 62B), and darkening with advanced senescence to a medium pink (RHS Red Purple Group 63C).
Length: Approximately 19 to 20 mm.
Petal claw:
*Form.*—The claw is considered truncate in shape and has a medium size when compared to other *Prunus persica* varieties.
*Length.*—Approximately 3 to 4 mm.
*Width.*—Approximately 2 to 3 mm.
Petal margins: Generally considered variable, from nearly smooth to highly undulate and ruffled, especially apically.
Petal apex: Generally — The petal apices appear slightly domed.
Flower pedicel:
*Length.*—Considered medium-short, and having an average length of approximately 2 to 3 mm.
*Thickness.*—Considered average, approximately 1 to 2 mm.
*Color.*—A medium green (RHS Yellow-Green Group 152A).
Floral nectaries:
*Color.*—Dull orange to orange-gold (RHS Greyed-Red Group 179A).
Calyx:
*Surface texture.*—Generally glabrous.
*Color.*—A dull red (approximately RHS Greyed-Red Group 181B).
Sepals:
*Surface texture.*—The surface has a short, fine, wooly and a gray-colored texture.
*Size.*—Average, and ovate in form.
*Color.*—A dull red (approximately RHS Greyed-Red Group 182B).
Anthers:
*General.*—Average in size for the species.
*Color.*—Red to reddish-orange (approximately RHS Grey Purple Group 185B).
Pollen production: Pollen is abundant, and has a yellow-gold color (approximately RHS Yellow Orange 19B).
Filaments:
*Size.*—Variable in length, approximately 11 to 15 mm, with the filaments generally slightly shorter than the pistil.
*Color.*—Pink with purple tinge (approximately RHS Red Purple Group 69D) and darkening with advanced maturity.
Pistil:
*General.*—Average in size, but slightly longer, relative to the general anther height, overall. The presence of dual or double pistils is common. Double pistils can commonly be represented in approximately 50% of the flowers.
*Length.*—Approximately 17 to 19 mm, including the ovary.
*Color.*—Very pale green (approximately RHS Yellow Green Group 150C).
Surface texture: The variety has a long, pale green (approximately RHS 150C) to whitish green (range from RHS Green White Group 157A to 157D) pubescent pistil.

4.6 FRUIT

Maturity when described: The present variety of fruit is described, as it is found in its firm ripe condition at full commercial maturity. Under the ecological conditions prevailing in the San Joaquin Valley of Central California:
*First picking.*—May 28, 2000.
*Last picking.*—Jun. 10, 2000.
Size: General — Medium to medium large for the season and considered uniform.
*Average cheek diameter.*—Approximately 73 to 72 mm.
*Average suture diameter.*—Approximately 68 to 70 mm.
*Average axial diameter.*—Approximately 69 to 72 mm.
Fruit form: Generally quite oblate in its lateral aspect. Occasionally the fruit exhibits less symmetry when comparing the suture height with the line opposite the suture. The fruit is generally uniform in symmetry when viewed from the apical aspect.
Fruit suture: Generally, the suture appears as a thin line that extends from the base to the apex, and appears slightly deeper at the apex, forming a shallow basin at the apical point. No apparent callusing or stitching exists along the suture line.
*Color.*—The suture normally is the same color as the underlying blush. Both the orange-yellow background (RHS Yellow Group 16B) and the red orange color (RHS Orange Red Group 34B) occur.
Ventral surface: Form — Considered uniform.
Stem cavity:
*Size.*—Considered moderately shallow for the species.
*Width.*—Approximately 7 to 10 mm.
*Length.*—Approximately 18 to 24 mm.
*Depth.*—Approximately 5 to 8 mm.
*Form.*—Considered narrowly oval.
Fruit base: Generally considered truncate in form, and uniform.
Fruit apex: Generally considered depressed and usually recessed below the height of the apical shoulders.
Fruit stem:
*Generally.*—Considered medium in length, approximately 6 to 8 mm.
*Thickness.*—Approximately 3 to 4 mm.
*Color.*—Generally a pale yellow-green (approximately RHS Yellow Green Group 145B).
Fruit skin: Generally considered medium or average in thickness.
*Surface texture.*—The variety has very light, short pubescence.
*Skin acidity.*—Considered neutral.
*Tenacious to flesh.*—Yes at commercial maturity.
*Tendency to crack.*—Not observed.
*Skin color.*—Generally — Variable, with approximately 40–65% of the fruit surface covered with an attractive orange red blush.
*Down.*—Light and short.
*Blush color.*—The blush color is generally more prevailing apically. This red blush ranges from an orange red (RHS Orange Red 34A to 30B) with many degrees of shading and blending occurring between these colorations. The type of blush coloration would be categorized as a striped, chimeric or tigered covering.
*Skin ground color.*—This is generally present in variable percentages covering approximately 35–60% of the fruit's surface. The skin ground is yellow-golden (approximately RHS Yellow Orange 21B).

Flesh color: Generally considered variable from a yellow/orange (RHS Yellow Orange Group 17C to 16B).

Flesh fibers: Present, numerous in number, and lightly colored. These fibers are present throughout the flesh.

Stone cavity color: Generally considered variable from a yellow/orange (RHS Yellow Orange Group 17C to 16B).

Flesh texture: Generally, the flesh is considered from and fine at commercial maturity.

Ripening: Generally the fruit of the present variety ripens evenly.

Flavor: Considered very sweet and a rich, with slightly acidic flavor.

Aroma: Pleasant and reasonably abundant.

Eating: Generally considered very good to excellent, particularly for an early ripening variety.

4.7 STONE

Attachment: Clingstone at commercial maturity.

Stone size: Generally considered medium to medium-large relative to the ratio of stone to fruit size.

*Length.*—Approximately 30 to 33 mm.

*Width.*—Approximately 25 to 27 mm.

*Thickness.*—Approximately 18 to 21 mm.

Fibers: Generally a few medium length fibers are attached along the entire surface of the stone.

Stone form: Generally the stone is considered oval.

Stone base: The stone is somewhat oblique.

Base angle: The base angle of the stone is variable, but most frequently is considered slightly oblique to the stone axis.

Hilum: Generally considered medium in size, and rather poorly defined as is common in very early ripening varieties. The hilum is approximately 4 to 5 mm long and 2 to 4 mm wide.

*Form.*—Considered oval.

Apex: Shape — The stone apex is raised and has an acute tip.

Stone shape: Considered variable. The stone normally is equal, although occasionally may appear unequal.

Stone surface:

*Surface texture.*—Generally considered medium to medium-smooth in roughness and exhibits substantial pitting laterally. Some moderate grooving is apparent over the apical shoulders. Surface pitting is prominent generally, and common throughout the stone surface.

*Ridges.*—Numerous fine ridges are present basally, and converge towards the base of the stone.

Ventral edge: Width — Considered medium to medium-small, and having a dimension of approximately 3.5 to 5 mm at the mid-suture.

Dorsal edge: Shape — Fruit, grooved, and having relatively smooth edges. The dorsal edge is moderately eroded over the apical shoulder.

Stone color: The color of the dry stone is a white-orange color (RHS Orange-White Group 159A). The color of the inside surface of the endocarp is primarily RHS Greyed Orange 164C and 164B.

Tendency to split: Splitting is relatively uncommon.

Kernel: The kernel fills the endocarp at harvest and measures approximately 5–6 mm in thickness, 8–10.5 mm in width, and 15.5–17 mm in length. When dried the shriveled kernels measure approximately 1 mm in thickness, 7 mm in width, and 14 mm in length. The colors of the shriveled kernels are primarily RHS Greyed Orange 164A and 165B.

Use: The subject variety, 'TROPICPEACHONE', is considered to be a peach tree of early-season maturity, which produces fruit which are very firm, attractively colored, and which are useful for both local and long distance shipping.

Keeping quality: Excellent.

Resistance to insects and disease: No particular susceptibilities were noted.

Shipping quality: Above average.

Although the new variety of peach tree possesses the described characteristics when grown under the ecological conditions prevailing near Fowler, Fresno County, Calif., it will be understood that variations of the usual magnitude and characteristics incident to the changes in growing conditions, fertilization, pruning, and pest control are to be expected.

We claim:

1. A new and distinct variety of *Prunus persica* plant, substantially as illustrated and described herein.

* * * * *